US011648021B2

(12) United States Patent
Krolik et al.

(10) Patent No.: US 11,648,021 B2
(45) Date of Patent: *May 16, 2023

(54) RETRIEVAL APPARATUS AND METHODS FOR USE

(71) Applicant: Incept, LLC, Mountain View, CA (US)

(72) Inventors: Jeffrey A. Krolik, Campbell, CA (US); Gwendolyn Watanabe, Sunnyvale, CA (US); James H. Dreher, Santa Monica, CA (US)

(73) Assignee: Incept, LLC, Mountain View, CA (US)

( * ) Notice: Subject to any disclaimer, the term of this patent is extended or adjusted under 35 U.S.C. 154(b) by 990 days.

This patent is subject to a terminal disclaimer.

(21) Appl. No.: 16/442,521

(22) Filed: Jun. 16, 2019

(65) Prior Publication Data

US 2019/0298395 A1    Oct. 3, 2019

Related U.S. Application Data

(63) Continuation of application No. 15/350,057, filed on Nov. 13, 2016, now Pat. No. 10,321,924, which is a
(Continued)

(51) Int. Cl.
*A61B 17/221* (2006.01)
*A61B 17/22* (2006.01)
(Continued)

(52) U.S. Cl.
CPC .. *A61B 17/221* (2013.01); *A61B 2017/00862* (2013.01); *A61B 2017/2212* (2013.01);
(Continued)

(58) Field of Classification Search
CPC ........ A61B 17/221; A61B 2017/00862; A61B 2017/22035; A61B 2017/22038;
(Continued)

(56) References Cited

U.S. PATENT DOCUMENTS 5,626,605 A * 5/1997 Irie .......................... A61F 2/01
                                                    623/1.1
5,944,738 A * 8/1999 Amplatz ............ A61B 17/0057
                                                    606/213
(Continued)

FOREIGN PATENT DOCUMENTS

DE     10049812 A1 *  4/2002  ........... A61B 17/221
DE     10049812 A1    4/2002
(Continued)

*Primary Examiner* — Amy R Weisberg
(74) *Attorney, Agent, or Firm* — BakerHostetler

(57) ABSTRACT

An apparatus and method for capturing material within a body lumen are disclosed. The apparatus includes a core wire extending from a proximal end to a distal tip, an actuator member defining a lumen for receiving at least a portion of the core wire, and a distal basket having a distal enclosed end fixed relative to the core wire and one or more elements extending from a proximal open end to a collar slidable on the core wire. The collar is slidable on the core wire within an interior of the distal basket such that, when the collar contacts the actuator member, the collar applies an inward force to direct the proximal open end of the distal basket radially inwardly.

20 Claims, 8 Drawing Sheets

Related U.S. Application Data continuation of application No. 12/746,920, filed as application No. PCT/US2008/086298 on Dec. 10, 2008, now Pat. No. 9,492,263.

(60) Provisional application No. 61/046,395, filed on Apr. 18, 2008, provisional application No. 61/012,722, filed on Dec. 10, 2007.

(51) Int. Cl.
 *A61F 2/01* (2006.01)
 *A61B 17/00* (2006.01)
 *A61M 1/36* (2006.01)

(52) U.S. Cl.
 CPC .............. *A61B 2017/22035* (2013.01); *A61B 2017/22038* (2013.01); *A61F 2002/016* (2013.01); *A61F 2002/018* (2013.01); *A61F 2230/0069* (2013.01); *A61M 1/3655* (2013.01)

(58) Field of Classification Search
 CPC ....... A61B 2017/2212; A61F 2002/016; A61F 2002/018; A61F 2230/0069; A61M 1/3655
 See application file for complete search history.

(56) References Cited

U.S. PATENT DOCUMENTS

| | | | |
|---|---|---|---|
| 6,066,149 | A | 5/2000 | Samson et al. |
| 6,096,053 | A | 8/2000 | Bates |
| 6,425,924 | B1 | 7/2002 | Rousseau |
| 6,695,865 | B2 | 2/2004 | Boyle et al. |
| 6,712,859 | B2 | 3/2004 | Rousseau et al. |
| 6,755,867 | B2 | 6/2004 | Rousseau |
| 7,578,830 | B2 | 8/2009 | Kusleika et al. |
| 7,909,862 | B2 | 3/2011 | Garrison et al. |
| 7,972,355 | B2 | 7/2011 | Bales |
| 8,092,485 | B2 | 1/2012 | Lapid |
| 8,562,643 | B2 | 10/2013 | Tekulve et al. |
| 9,308,007 | B2 | 4/2016 | Cully et al. |
| 2002/0111648 | A1 | 8/2002 | Kusleika et al. |
| 2003/0040772 | A1 | 2/2003 | Hyodoh et al. |
| 2003/0060843 | A1 | 3/2003 | Boucher |
| 2003/0153943 | A1 | 8/2003 | Michael et al. |
| 2004/0254594 | A1 | 12/2004 | Alfaro |
| 2005/0267523 | A1 | 12/2005 | Devellian et al. |
| 2008/0275485 | A1 | 11/2008 | Bonnette et al. |
| 2010/0106182 | A1 | 4/2010 | Patel et al. |
| 2011/0137335 | A1 | 6/2011 | Hallisey |
| 2015/0320431 | A1 | 11/2015 | Ulm, III |
| 2017/0143465 | A1 | 5/2017 | Ulm, III |
| 2017/0150979 | A1 | 6/2017 | Ulm, III |
| 2017/0172591 | A1 | 6/2017 | Ulm, III |
| 2017/0265877 | A1 | 9/2017 | Ulm, III |
| 2017/0290600 | A1 | 10/2017 | Ulm, III |
| 2018/0008295 | A1 | 1/2018 | Ulm, III |
| 2018/0271548 | A1 | 9/2018 | Ulm et al. |

FOREIGN PATENT DOCUMENTS

| | | |
|---|---|---|
| WO | 00/53120 A1 | 9/2000 |
| WO | 01/97697 A1 | 12/2001 |
| WO | 2009/076482 A1 | 6/2009 |

\* cited by examiner

RETRIEVAL APPARATUS AND METHODS FOR USE

RELATED APPLICATIONS

This application is a continuation of U.S. patent application Ser. No. 15/350,057, filed Nov. 13, 2016, and published as U.S. Patent App. Pub. No. 2017/0056034 on Mar. 2, 2017, which is a continuation of U.S. patent application Ser. No. 12/746,920, filed Jun. 8, 2010, and published as U.S. Patent App. Pub. No. 2010/0268265 on Oct. 21, 2010, which is a National Stage Entry of International Patent App. No. PCT/US2008/086298, filed Dec. 10, 2008, and published as International Patent App. Pub. No. WO 2009/076482 on Jun. 18, 2009, which claims the benefit of both U.S. Provisional Patent App. Nos. 61/12,722, filed Dec. 10, 2007, and 61/046,395, filed Apr. 18, 2008, the entire disclosures of which are expressly incorporated by reference herein.

FIELD OF THE INVENTION

The present invention relates generally to apparatus for retrieving material within a body lumen of a patient. More particularly, the present invention relates to expandable and/or contractible apparatus for retrieving thrombus, objects, or other material within a body lumen, such as a blood vessel, aorto-venous fistula, tubular graft, and/or other body lumen within a patient's body, and to methods for making and using such apparatus.

BACKGROUND

Flow within a blood vessel or other body lumen within a patient's vasculature may be constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Accordingly, apparatus and methods for removing material from aorto-venous grafts, e.g., to extend the useful life of such grafts, and/or from other blood vessels or body lumens would be useful.

SUMMARY

The present invention is directed to apparatus for retrieving material within a body lumen of a patient, and, more particularly, to expandable and/or contractible apparatus for retrieving thrombus or other material within a body lumen, such as a blood vessel, aorto-venous fistula, and/or other body lumen within a patient's body, and to methods for making and using such apparatus.

In accordance with a first embodiment, an apparatus is provided for removing, retrieving, or otherwise capturing material within a body lumen that includes a shaft or other elongate member including a proximal end, a distal end sized for introduction into a body lumen, and terminating in a distal tip; and a basket device carried on the distal end.

The basket device generally includes a distal basket adjacent the distal tip and a proximal basket proximal to and spaced apart from the distal basket. Each of the baskets may include an open end communicating with an interior of the respective basket, the open ends oriented towards one another. At least one of the proximal and distal baskets may be movable towards the other for substantially enclosing and capturing material within the interiors of the baskets. Thus, the basket device may include an open region between the proximal and distal baskets that may be substantially enclosed when the proximal and distal baskets are directed towards one another.

For example, the elongate member may include a core wire carrying the distal basket, and an actuator member adjacent the core wire carrying the proximal basket. Thus, axial movement of the actuator member and core wire relative to one another may direct the proximal basket distally towards the distal basket and/or direct the distal basket proximally towards the proximal basket. In one embodiment, the actuator member may be a tubular body surrounding the core wire such that the core wire extends distally from a distal end of the tubular body. The core wire may be pulled proximally at least partially into the tubular body, or the tubular body may be advanced distally at least partially over the core wire to enclosed the basket device.

In one embodiment, the proximal and distal baskets are expandable from a contracted condition, e.g., sized for introduction into a body lumen, and an expanded condition sized, e.g., for contacting a wall of the body lumen and/or for capturing material within the open ends of the baskets.

In addition or alternatively, each of the proximal and distal baskets may include a circumferential wall and a closed end opposite the open end. The circumferential wall may include a plurality of openings therein, e.g., by forming the baskets from a mesh structure, such as a laser-cut tube or a wire mesh.

In one embodiment, the basket device includes a middle portion extending between the proximal and distal baskets. The middle portion, e.g., a mesh tubular structure that may partially engage material captured between the baskets, may have a cross-section that is smaller than the proximal and distal baskets in the expanded condition. The middle portion may be coupled to the proximal and distal baskets such that the middle portion may be directed laterally, e.g., to accommodate material being received between the baskets adjacent the middle portion. For example, the middle portion may be coupled to the baskets by a plurality of struts, e.g., extending between ends of the middle portion and the open ends of the proximal and distal baskets. The middle portion may be substantially flexible such that the middle portion is compressible axially when the proximal and distal baskets are moved towards one another for capturing material within the interiors of the baskets. For example, the struts may bend or otherwise deflect to accommodate the middle portion being received within the interiors of the baskets as the baskets are directed towards one another.

Optionally, the apparatus may include a sheath or other tubular member, e.g., for selectively covering and/or exposing the basket device. The tubular member may include a proximal end, a distal end sized for introduction into a body lumen, and a lumen extending between the tubular member proximal and distal ends. Before use, the basket device may be disposed within the lumen in the contracted condition, e.g., adjacent the distal end of the tubular member, such that the elongate member extends proximally within the lumen.

The elongate member may be movable relative to the tubular member for deploying the basket device from the tubular member distal end. For example, the basket device may be directable to a contracted condition for placement within the tubular member lumen, and biased to resiliently expand to an expanded condition upon being deployed from the tubular member.

In addition or alternatively, the apparatus may include one or more actuators for selectively expanding and/or compressing the basket device between the contracted and expanded conditions. For example, the elongate member may include one or more balloons or other expandable members within the basket device that may be expanded to expand the basket device from the contracted to the expanded condition.

In accordance with another embodiment, an apparatus is provided for retrieving material within a body lumen that includes a core wire including a proximal end and a substantially atraumatic distal tip, and an actuator member adjacent the core wire and including a distal end disposed proximal to the distal tip. A distal basket is fixed axially relative to the core wire adjacent the distal tip and a proximal basket fixed axially relative to the distal end of the actuator member. The distal basket may include a proximal open end and a distal enclosed end defining an interior of the distal basket, and the proximal basket may include a distal open end and a proximal enclosed end defining an interior of the proximal basket. The basket device also includes a middle portion extending between the proximal and distal baskets. The middle portion may have a cross-section that is smaller than the proximal and distal baskets in the expanded condition.

The actuator member is movable distally relative to the core wire, e.g., to direct the proximal basket distally towards the distal basket, for substantially enclosing and capturing material within the interiors of the baskets. The middle portion may be compressible axially when the proximal basket is moved distally towards the distal basket, e.g., to accommodate receiving the middle portion within the interiors of the baskets along with material captured therein.

In accordance with yet another embodiment, an apparatus is provided for retrieving material within a body lumen that includes a core wire comprising a proximal end and a substantially atraumatic distal tip; and an actuator member adjacent the core wire and comprising a distal end disposed proximal to the distal tip, the actuator member movable distally relative to the core wire. A distal basket is fixed axially relative to the core wire adjacent the distal tip, the distal basket comprising a proximal open end and a distal enclosed end defining an interior of the distal basket; and a proximal basket fixed axially relative to the distal end of the actuator member, the proximal basket comprising a distal open end and a proximal enclosed end defining an interior of the proximal basket, the proximal basket movable distally towards the distal basket when the actuator member is moved distally relative to the core wire for substantially enclosing and capturing material within the interiors of the baskets. An actuator collar is slidable on the core wire within the interior of the distal basket, the collar coupled to the open end of the distal basket such that, when the actuator member is moved distally relative to the core wire, the collar applies an inward force to direct the open end of the distal basket radially inwardly.

In accordance with still another embodiment, a method is provided for removing, retrieving, or otherwise capturing material within a body lumen of a patient. A basket device may be introduced into the body lumen in a contracted condition, the basket device including a proximal basket and a distal basket spaced apart from one another. Each of the proximal and distal baskets may include an open end communicating with an interior of the respective basket, the open ends oriented towards one another. The distal basket may be deployed such that the distal basket expands within the body lumen and the open end is disposed distal to material to be removed, and the proximal basket may be deployed such that the proximal basket expands within the body lumen and the open end is disposed proximal to material to be removed. At least one of the proximal and distal baskets may be directed towards the other to capture the material through the open ends into interiors of the proximal and distal baskets.

In accordance with yet another embodiment, a method for retrieving, removing, or otherwise capturing material within a body lumen of a patient. A basket device is introduced into the body lumen, e.g., in a contracted condition. The basket device may include a proximal basket and a distal basket spaced apart from one another, each of the proximal and distal baskets including an open end communicating with an interior of the respective basket, the open ends oriented towards one another. The distal basket may be deployed such that the distal basket expands within the body lumen and the open end is disposed distal to material to be removed, and the proximal basket may be deployed such that the proximal basket expands within the body lumen and the open end is disposed proximal to material to be removed, e.g., after deploying the distal basket. At least one of the proximal and distal baskets may be directed towards the other to capture the material through the open ends into interiors of the proximal and distal baskets.

In one embodiment, the open end of the distal basket may be directed radially inwardly as the at least one of the proximal and distal baskets towards the other. For example, the at least one of the proximal and distal baskets may be directed towards the other until the open end of the distal basket is directed radially inwardly and received within the open end of the proximal basket.

Optionally, the proximal basket may be directed at least partially into a lumen of a tubular device, e.g., before withdrawing the tubular device from the body lumen. For example, the proximal basket may be directed entirely into the lumen of the tubular device, e.g., thereby compressing the proximal basket being radially inwardly as the proximal basket is directed into the lumen of the tubular device. In addition, the proximal basket may at least partially compress the distal basket radially inwardly when the proximal basket is directed into the lumen of the tubular device, e.g., allowing the distal basket to be directed into the lumen of the tubular device after the proximal basket is directed into the lumen of the tubular device.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments, in which.

DETAILED DESCRIPTION OF THE EXEMPLARY EMBODIMENTS

Figure 1:
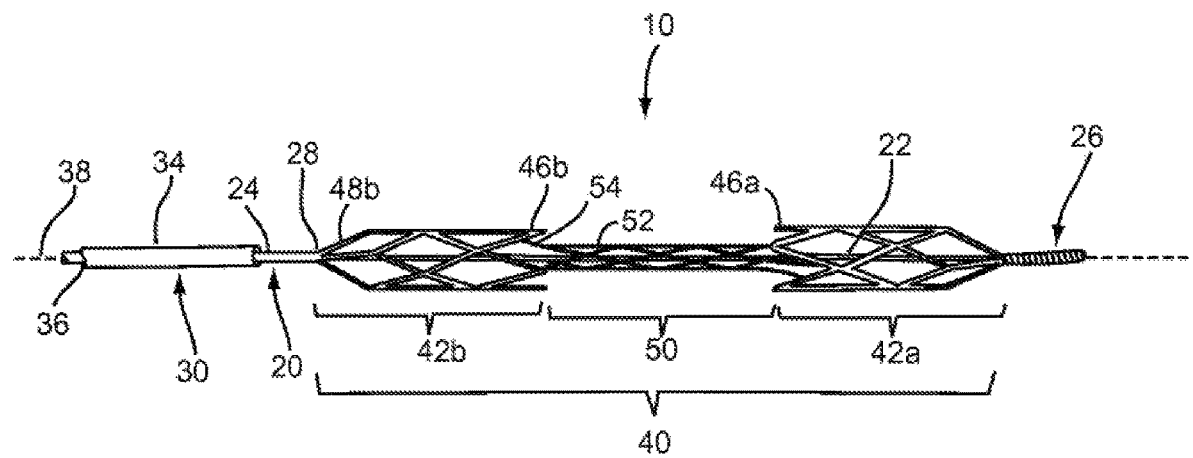
FIG. 1 is a side view of a distal end of a first embodiment of an apparatus for capturing material from within a body lumen.

Turning to the drawings, FIG. 1 shows an exemplary embodiment of an apparatus 10 for removing, retrieving, and/or otherwise capturing thrombus, objects, or other material from within a body lumen, such as a blood vessel, aorto-venous fistula, tubular graft, and the like (not shown). Generally, the apparatus 10 includes an expandable basket device 40 carried by a shaft or other elongate member 20, and a sheath or other tubular member 30 for facilitating delivery and/or removal of the shaft 20 and basket device 40.

In the embodiment shown, the shaft 20 includes a core wire 22 and an actuator member 24 disposed adjacent the core wire 22 that are movable axially relative to one another, the shaft 20 generally defining a central longitudinal axis 38 for the apparatus 10. The core wire 22 may be a substantially flexible elongate member, e.g., a solid or hollow wire structure including a proximal end (not shown) and a distal end terminating in a distal tip 26. As shown, the distal tip 26 may be substantially atraumatic, e.g., covered by a coiled wire and/or a polymeric covering, and/or may include a "J" or other rounded shape (not shown) to minimize risk of perforation or catching during advancement within a patient's body.

The actuator member 24 may be an elongate tubular body including a proximal end (not shown), a distal end 28 having a size for introduction into a body lumen, and a lumen 29 extending therebetween. The core wire 22 may be slidably received within the lumen 29 such that the core wire 22 extends from the lumen 29 beyond the distal end 28 and the distal tip 26 is spaced apart from the distal end 28 of the actuator member 24. Alternatively, the actuator member 24 may be another elongate member, e.g., a wire or other rail (not shown) disposed adjacent to the core wire 22, as long as the actuator member 24 and core wire 22 are movable axially relative to one another.

The core wire 22 and actuator member 24 may have sufficient length to extend from a target site within a patient's body to a location outside the patient's body. Alternatively, the core wire 22 and/or actuator member 24 may extend to and be coupled to other components of the apparatus 10 spaced apart from the basket device 40. The core wire 22 and/or actuator member 24 may have sufficient column strength to allow advancement of the core wire 22 and/or actuator member 24 without substantial risk of buckling or kinking. For example, a distal region of the core wire 22 and actuator 24 may be relatively flexible and a proximal region may be substantially rigid or semi-rigid to facilitate advancement of the distal region from the proximal end of the apparatus 10. The core wire 22 may be formed from a single wire strand, multiple strands, a coiled wire structure, and the like having a sufficiently small profile to be slidable received in the actuator member 24. The actuator member 24 may be a formed from a hypotube, a multiple layer catheter structure, e.g., including a braid or other reinforcement and the like.

In an exemplary embodiment, the proximal ends of the core wire 22 and actuator member 24 may be received within and/or otherwise coupled to a handle (not shown). The handle may include an actuator, e.g., a slider control, button, and the like (not shown) for directing one of the core wire 22 and actuator member 24 axially relative to the other, as explained further below. In addition or alternatively, the handle may include one or more additional controls or actuator. For example, the handle may include an actuator for retracting the sheath 30 relative to the basket device 40 (or advancing the basket device 40 relative to the sheath 30), also as described further below.

The basket device 40 carried by the shaft 20 generally includes a distal basket 42a adjacent the distal tip 26, and a proximal basket 42b proximal to and spaced apart from the distal basket 42a. For example, the distal basket 42a may be attached to or otherwise fixed axially relative to the core wire 22, e.g., adjacent the distal tip 26, and the proximal basket 42b may be attached to or otherwise fixed axially relative to the actuator member 24, e.g., to the distal end 28. In addition, in the embodiment shown, the basket device 40 includes a middle portion 50 that extends between the distal and proximal baskets 42a, 42b.

As shown in FIG. 1, each of the baskets 42 includes a circumferential wall 44 defining an open end 46 communicating with an interior of the basket 42 and a closed end 48 attached to the core wire 22 or actuator member 24. The open ends 46 are oriented towards one another and initially spaced apart from one another, as shown in FIG. 1. Initially, the distance between the open ends 46 may be between about five and fifty millimeters (5-50 mm), e.g., to provide sufficient space between the baskets 42 to facilitate receiving material between the baskets 42 for retrieval. When the actuator member 24 and core wire 22 are moved axially relative to one another, the baskets 42 may be moved towards the other for substantially enclosing and capturing material within the interiors of the baskets 42, e.g., as shown in FIGS. 2C-2E and described further below. In addition or alternatively, the space between the baskets 42 may be adjusted by the user, e.g., to increase or decrease the distance between the open ends 46 before deploying the baskets 42.

In one embodiment, the baskets 42 may be expandable from a contracted condition (not shown), e.g., sized for introduction through a patient's vasculature or other passages into a body lumen, and an expanded condition (shown in FIG. 1), e.g., for capturing material within the open ends 46 of the baskets 42. For example, the baskets 42 may be formed from elastic or superelastic material, such that the baskets 42 may be compressed radially inwardly to the contracted condition and resiliently expand towards the expanded condition.

Alternatively, the baskets 42 may be actuatable, i.e., selectively expanded and/or contracted using one or more actuators (not shown) on the proximal end of the apparatus 10. For example, one or more balloons or other expandable members (not shown) may be provided on the core wire 22 within the baskets 42. The balloon(s) may allow the baskets 42 to be expanded separately from one another and/or simultaneously depending upon the number of balloons and/or inflation lumens provided in the core wire 22.

The middle portion 50 extends between the distal and proximal baskets 42a, 42b and has a cross-section that is smaller than the proximal and distal baskets in the expanded condition. As shown, the middle portion 50 is a tubular structure that includes opposite ends 52 coupled to the respective baskets 42, e.g., by a plurality of struts 54. For example, as shown in FIG. 1, the struts 54 may be coupled to the ends 52 of the middle portion 50 and adjacent the open ends 46 of the distal and proximal baskets 42*a*, 42*b*. The struts 54 may be sufficiently flexible such that the middle portion 50 is movable laterally away from the central axis 38 relative to the distal and proximal baskets 42*l*, 42*b*, for example, to accommodate receiving material within a body lumen between the baskets 42 adjacent the middle portion 50, e.g., as shown in FIG. 2C.

In addition, the middle portion 50 may be substantially flexible such that the middle portion 50 is compressible axially, e.g., when the baskets 42 are moved towards one another for capturing material within the interiors of the baskets 42. In addition or alternatively, the struts 54 may be substantially flexible to provide hinges that facilitate receiving the middle portion 50 within the interiors of the baskets 42 as the baskets 42 are moved towards one another.

The middle portion 50 may define a passage axially therethrough through which the core wire 22 may extend. Alternatively, the core wire 22 may extend along an exterior of or otherwise adjacent the middle portion 50.

The wall 44 of the baskets 42 and/or the middle portion 50 may be porous or otherwise include a plurality of openings 47 therein, e.g., to allow fluid to flow around and/or through the baskets 42 during use. For example, the baskets 42 may be formed from one or more hypotubes or other tubular bodies that have portions of the bodies removed, e.g., by laser cutting, etching, mechanical cutting, and the like to define a plurality of struts 45 surrounding the openings 47. For example, if the actuator member 24 is formed from a hypotube or other tubular material, the proximal basket 42*b* may be formed by cutting openings 47 and/or struts 45 in an end of the tubular material and then bending the resulting structure into the shape of the proximal basket 42*b*. Similarly, the middle portion 50 may also be formed from a tubular body that has portions removed to create a plurality of struts surrounding openings in the middle portion 50.

Alternatively, the baskets 42 and/or middle portion 50 may be made from one or more wires that are formed into a mesh structure, e.g., by welding, bonding, or otherwise attaching the wire(s) together to define the struts 45. Exemplary materials for the baskets 42 include metals, such as Nitinol or stainless steel, polymers or other plastics, or composite materials. The baskets 42 may be heat treated or otherwise set to be biased to the expanded condition yet resiliently compressible to the contracted condition. For example, if the baskets 42 are formed by cutting openings 47 and/or struts 45 from individual tubular bodies having a cross-section similar to the contracted condition, the resulting structure may be expanded to the expanded condition and then heat treated to program the expanded condition into the material of the structure.

Optionally, if smaller apertures are desired, a covering (not shown) may be placed over or within one or both of the baskets 42. Holes may be drilled, cut, or otherwise provided in the covering, e.g., using laser drilling, mechanical drilling, punching, and the like to provide a desired pore size. The covering may be attached to the basket(s) 42 by bonding with adhesive, heat fusion, sonic welding, interference fit, and the like. Alternatively, a non-porous covering may be provided if flow obstruction through the wall 44 of the basket(s) 42 is desired.

As shown in FIG. 1, the baskets 42 and middle portion 50 may be defined by a plurality of zigzag struts that extend circumferentially and/or axially around the basket device 40. For example, alternating diagonal struts may be connected to one another about the circumference of the baskets 42 to define a zigzag band and adjacent bands may be attached or integrally formed together in an axially repeated pattern. For example the open ends 46 of the baskets 42 may define a zigzag pattern extending around a perimeter of the open ends 46. In one embodiment, the zigzag patterns of at least the open ends 46*a*, 46*b* may be out of phase with one another such that the open ends 46 may at least partially intertwine with one another to substantially enclose the interiors of the baskets 42, e.g., as described further below.

After forming the baskets 42 and middle portion 50, the struts 54, which may be integrally formed with the middle portion 50 or formed separately and attached to the ends 52 of the middle portion 50, e.g., by welding, bonding, and the like, may be attached to the baskets 42 adjacent the open ends 46 using similar methods. It may be useful to attach the struts 54 extending from the ends 52 of the middle portion 50 adjacent the open ends 46 (rather than at the open ends 46 themselves) to allow the open ends 46 of the baskets 42 to remain free during use, e.g., when the baskets 42 are deployed and directed towards one another to capture material within the baskets 42.

In exemplary embodiments, the baskets 42 may have a diameter between about half and two millimeters (0.5-2.0 mm) in the contracted condition and a diameter between about two and nine millimeters (2.0-9.0 mm) in the expanded condition. The middle portion 50 may have a diameter between about one and three millimeters (1-3 mm). For example, the middle portion 50 may have a diameter slightly smaller than the contracted condition, e.g., to accommodate overlap with the baskets 42, and the diameter of the middle portion 50 may remain substantially constant upon expansion of the baskets 42. Alternatively, the middle portion 50 may be radially compressed into a diameter substantially smaller than the contracted condition of the baskets 42 and may be expanded to a diameter smaller than the expanded condition of the baskets 42.

Figure 2A:
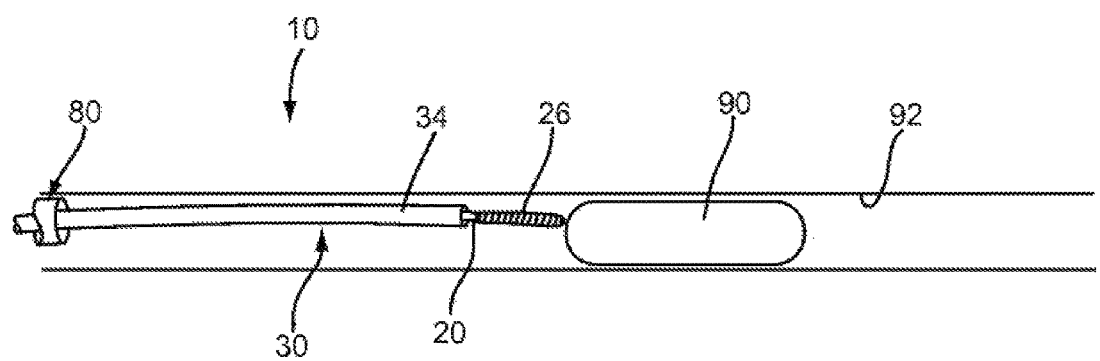
FIGS. 2A-2E are cross-sectional views of a body lumen showing a method for capturing material from the body lumen using the apparatus of FIG. 1.
Figure 2B:
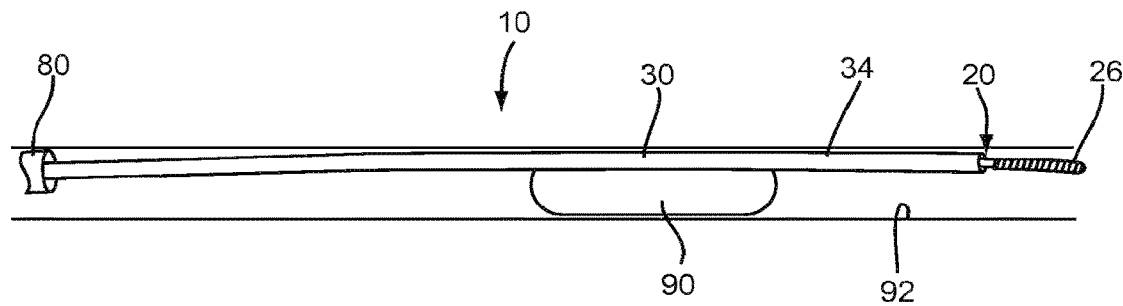
Figure 2C:
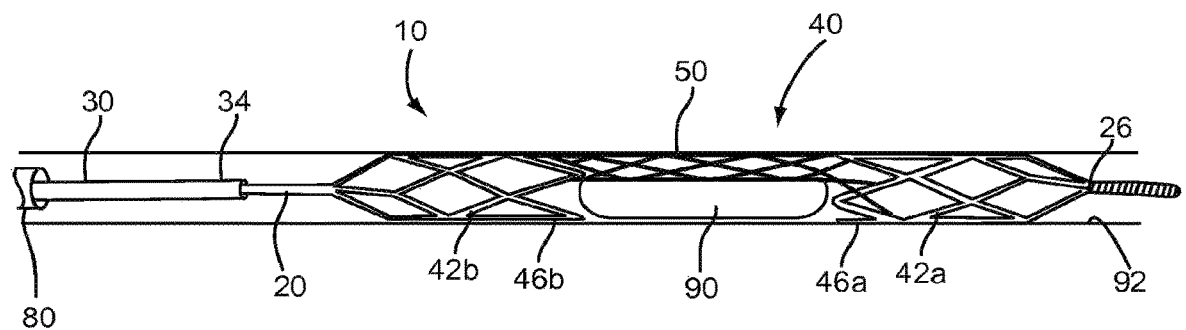
Figure 2D:
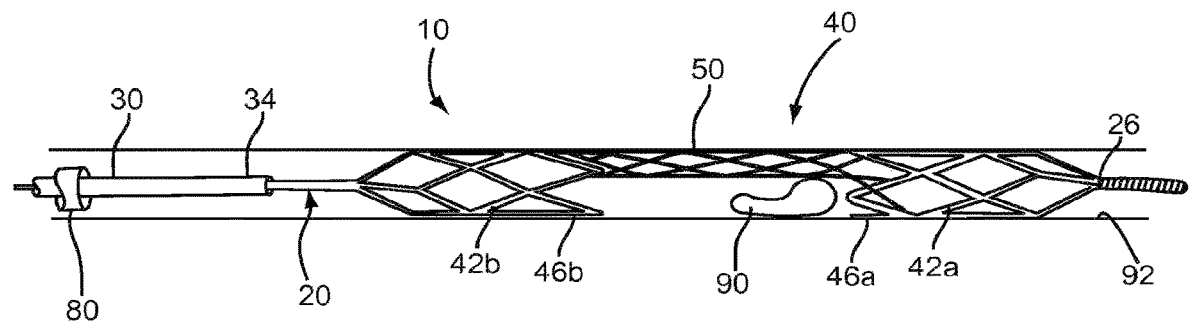
Figure 2E:
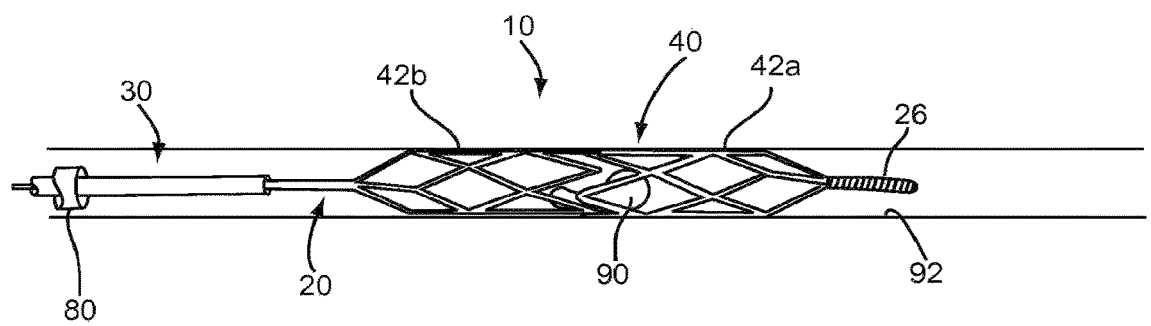

As shown in FIGS. 2A and 2B, the shaft 20 and/or basket device 40 may be carried within the sheath 30, e.g., to facilitate delivery of the basket device 40 to a target site. The sheath 30 may include a proximal end (not shown), a distal end 34, and a lumen 36 extending therebetween. Optionally, the sheath 30 may include one or more additional lumens (not shown) extending between the proximal end and the distal end 34, e.g., for delivering and/or aspirating fluid via the distal end 34, for receiving a guidewire or other rail (not shown), and the like. For example, in some applications, it may be desirable to advance the entire apparatus 10 over a guidewire or other rail (not shown), e.g., by loading the guidewire through a guidewire lumen (also not shown) disposed adjacent the lumen 36. In addition, or alternatively, a source of fluid, e.g., one or more solvents or other therapeutic agents, a source of vacuum, e.g., a syringe, and the like, may be coupled to the sheath 30.

For example, as described above, the apparatus 10 may include a handle (not shown), and the proximal end of the sheath 30 may be coupled to the handle such that the sheath 30 and/or the shaft 20 are movable axially relative to one another to accommodate deploying and/or recovering the basket device 40 during use. In addition, the handle may include one or more ports (also not shown) for being coupled to a source of fluid and/or vacuum. The port(s) may communicate with the lumen 36 (or other lumen, not shown, provided in the sheath 36).

During assembly or immediately before use, the shaft 20 and/or basket device 40 may be loaded into the lumen 36 of the sheath 30, e.g., such that the basket device 40 is compressed into the contracted condition. For example, the shaft 20 may be backloaded into the sheath 30 until the baskets 42 are disposed adjacent the distal end 34 of the sheath. The baskets 42 may then be compressed into the contracted condition and directed into the lumen 36, e.g., such that the baskets 42 are disposed adjacent the sheath distal end 34 with the distal tip 26 extending from the sheath 30, as shown in FIGS. 2A and 2B. An external constraint (not shown) may be used to compress the baskets 42 inwardly before being loaded into the sheath 30. Alternatively, for at least the proximal basket 42b, the closed end 48b may be tapered or otherwise shaped to allow the closed end 48b to slidably engage the sheath distal end 34, thereby compressing the proximal basket 42b inwardly as the basket device 40 is pulled into the sheath 30.

The proximal ends of the core wire 22, actuator member 24, and/or sheath 30 may be coupled to any other necessary components of the apparatus 10, e.g., to a handle and/or actuator components, to provide an assembled apparatus 10 that may be provided to a user.

The baskets 42 (and/or middle portion 50) may be biased to resiliently expand to the expanded condition upon being deployed from the sheath 30. For example, as each of the baskets 42 become exposed, e.g., first the distal basket 42a and then the proximal basket 42b (as described further below), the baskets 42 may automatically and sequentially open towards the expanded condition. Alternatively, the baskets 42 may be selectively expandable from the contracted to the expanded conditions, e.g., by activating an actuator on a proximal end of the apparatus 10.

If desired, the apparatus 10 may include one or more markers to facilitate positioning and/or advancement of the apparatus 10 during use. For example, one or more radiopaque markers may be placed on the basket device 10, e.g., on the open ends 46 of the baskets 42. In addition or alternatively, such markers may be placed at one or more locations on the core wire 22, shaft 24, and/or sheath 40. Alternatively, the basket device 10 or components thereof may be formed from radiopaque or other materials that may facilitate imaging the apparatus 10 during use. For example, radiopaque markers and/or materials may facilitate positioning or otherwise imaging the apparatus 10 using fluoroscopy or other x-ray imaging, e.g., when deploying and/or actuating the basket device 40. Alternatively, echogenic markers and/or materials may be provided to facilitate imaging using ultrasound or similar imaging techniques.

Turning to FIGS. 2A-2E, an exemplary method is shown for retrieving, removing, or otherwise capturing material 90 within a body lumen 92, e.g., using an apparatus 10, which may be any of the embodiments described herein, and not necessarily limited to the embodiment shown and described below with reference to FIG. 1. The body lumen 92 may be a blood vessel, e.g., a vein or artery, a graft, e.g., an aorto-venous fistula, tubular xenograft, or synthetic tubular graft, and the like. For example, the body lumen 92 may be a passage communicating between an adjacent artery and vein (not shown), e.g., in an arm or other region of a dialysis patient. Alternatively, the body lumen 92 may be a blood vessel within a patient's vasculature, e.g., a peripheral vessel in a patient's leg, a cerebral vessel, and the like. In a further alternative, the material 90 may be a stone within a patient's urinary tract or other foreign object to be removed from the patient's body.

Optionally, the body lumen 92 may be accessed using one or more additional instruments (not shown), which may be part of a system or kit including the apparatus 10. For example, an introducer sheath or other tubular member (not shown) may be introduced adjacent the target site where the material is to be removed, or may be introduced elsewhere in the patient's body to provide access to the patient's vasculature or other passages communicating with the body lumen 92. If the body lumen 92 is located in a peripheral vessel of the patient, a percutaneous puncture or cut-down may be created using a needle or other instrument (not shown) at a peripheral location (also not shown), such as a femoral artery, carotid artery, or other entry site, and an introducer sheath may be placed through the puncture at the peripheral location to provide access. The apparatus 10 may be advanced through the patient's vasculature from the entry site, e.g., alone or with the aid of a guide catheter 80, guidewire (not shown), and the like.

For example, to facilitate directing the apparatus 10 from an entry site to the target body lumen 92, a guide catheter, micro-catheter, or other tubular body 80 may be placed from the entry site to the body lumen 92 using conventional methods. In addition or alternatively, a guidewire (not shown) may be placed from the entry site to the body lumen 92 if desired, e.g., if the apparatus 10 includes a guidewire lumen in the sheath 30 or core wire 22.

Initially, as shown in FIG. 2A, the apparatus 10 has been advanced through the guide catheter 80 into the body lumen 92. The apparatus 10 may be provided with the basket device 40 (not shown) compressed and/or retracted into the sheath 20, i.e., in the contracted condition. For example, the basket device 40 may be placed within the sheath 20 during manufacturing or immediately before the procedure by the user. The relatively low profile of the sheath 30 and atraumatic distal tip 26 may facilitate advancing the apparatus 10 adjacent the material 90, e.g., such that the distal tip 26 and distal end 34 of the sheath 30 may be advanced through or along and distally beyond the material 90, as shown in FIG. 2B, without substantial risk of dislodging, breaking, or otherwise damaging the material 90.

Optionally, the guide catheter 80 and/or sheath 30 may facilitate delivering one or more fluids into the body lumen 92, e.g., to facilitate imaging and/or positioning the apparatus 10. For example, radiopaque fluid may be delivered into the body lumen 92 via the guide catheter 80 (or via a lumen in the sheath 30, actuator member 24, or core wire 22) to facilitate locating and/or measuring the size of the material 90 using fluoroscopy. Markers (not shown) on the apparatus 10 may facilitate positioning the basket device 40 relative to the material 90 before deployment. For example, such markers may facilitate verifying that the basket device 40 is positioned with the distal basket 42a distal to the material 90 and the proximal basket 42b proximal to the material 90, e.g., with the material adjacent the middle portion 50, as shown in FIGS. 2B and 2C, before deployment. If desired, the spacing of the distal and proximal baskets 42a, 42b may be adjusted based upon the size of the material 90 encountered. For example, if the length of the material 90 is greater than the initial spacing of the baskets 42 within the sheath 30, the core wire 22 or actuator member 24 may be directed axially to increase the spacing between baskets 42 to ensure that the open ends are located proximally and distally sufficiently from the material 90 upon deployment.

The basket device 40 may then be deployed within the body lumen 92, e.g., such that the material to be removed or captured is disposed within or adjacent the basket device 40, as shown in FIG. 2C. For example, the sheath 30 may be retracted, thereby deploying the distal basket 42a beyond the material 90 and then deploying the proximal basket 42b proximal to the material 90. As described above, the baskets 42 may resiliently and/or automatically expand upon being exposed within the body lumen 92. In addition or alternatively, the baskets 42 may be selectively expanded within the body lumen 92. For example, a balloon or other expandable member (not shown) may be expanded to expand the baskets 42 independently of one another or simultaneously. In the expanded condition, the open ends 46 may substantially engage or contact the wall of the body lumen 92, e.g., to prevent material 90 captured between the proximal and distal baskets 42 from being released.

As shown, the middle portion 50 of the basket device 40 may be disposed adjacent the material 90 upon deployment, e.g., being pushed laterally to one side of the body lumen 92 by the material 90. For example, the struts 54 connecting the middle portion 50 to the baskets 42 may bend or otherwise provide sufficient flexibility to accommodate this lateral movement of the middle portion 50, if desired. The openings in the middle portion 50 may partially capture or engage the material 90, e.g., to at least partially secure the material 90 to the middle portion 50, which may reduce the risk of material 90 breaking free from the basket device 40. Optionally, if desired, the middle portion 50 may include other structures and/or materials, e.g., strands, fibers, and the like (not shown), in addition to or instead of the tubular structure shown, which may enhance securing the material 90 to the middle portion 50.

Turning to FIG. 2D, if desired, the material 90 may be treated, e.g., at least partially dissolved, macerated, and the like before or after actuation of the basket device 40. For example, a therapeutic agent may be delivered into the body lumen 92 via the guide catheter 80 (or an infusion lumen in one of the members of the apparatus 10). The middle portion 50 of the basket device 40 may ensure a passage through and/or beyond the material 90, which may enhance treatment of the material 90 along its entire length within the body lumen 92. The porous, open configuration of the basket device 40 may also facilitate such treatment of the material 90. For example, if the material 90 is thrombus or other relatively soft material, the material 90 may be compressed within the basket device 40 such that portions of the material 90 pass through the openings 47 in the basket device 40. This may increase exposed surface area of the material 90 increasing the effectiveness of any therapeutic agent introduced into the body lumen 92. Optionally, vacuum may be applied via the guide catheter 80 (or one of the members of the apparatus 10), e.g., to aspirate any therapeutic agent(s), dissolved or separated material 90, and the like, before or after actuating the basket device 40.

In addition, if the middle portion 50 is a tubular structure, the middle portion 50 may provide a flow passage across the material 90. For example, if the material 90 is clot, thrombus, and the like partially or entirely obstructing the body lumen 92, deployment of the middle portion 50 may immediately provide a flow path for blood across the material 90. Such blood flow may reduce or eliminate an ischemic condition of tissues downstream from the obstruction or provide other immediate benefit to the patient.

Turning to FIG. 2E, the basket device 40 may then be actuated to capture the material 90 within the baskets 42, e.g., to minimize liberation of the material 90 during removal. For example, the core wire 22 may be directed proximally, thereby pulling the distal basket 42a towards the proximal basket 42b, e.g., until the open ends 46 contact or are otherwise disposed immediately adjacent one another. Alternatively, the actuator member 24 may be directed distally to push the proximal basket 42b distally towards the distal basket 42a. As shown, the zigzag shapes of the open ends 46 are offset from one another such that the baskets 42 may engage or become entwined with one another to enhance entrapment of the material 90 within the basket device 40. Optionally, the open ends 46 may include detents or other features that may lock or otherwise secure the open ends 46 together to prevent subsequent separation of the baskets 42. The struts 54 and/or the middle portion 50 may bend or otherwise deform to facilitate receiving the middle portion 50 within the interiors of the baskets 42 along with the material 90 captured therein.

The apparatus 10 may then be withdrawn from the body lumen 92 along with the material 90 captured within the basket device 40. For example, the apparatus 10 may be pulled until the proximal basket 42b contacts the guide catheter 80, whereupon the guide catheter 80 and apparatus 10 may be withdrawn from the body lumen 92 and/or entirely from the patient's body. Alternatively, the apparatus 10 may be directed such that the basket device 40 at least partially enters the guide catheter 80. For example, the closed end 48b of the proximal basket 42b may be tapered, as shown, thereby causing the proximal basket 42b to compress radially inwardly towards the contracted condition as it is directed into the guide catheter 80. If the open ends 46 of the baskets 42 are sufficiently entwined, as the proximal basket 42b is compressed, the distal basket 42a may also become compressed, thereby allowing the entire basket device 40 to be compressed and pulled into the guide catheter 80 with the material 90.

In addition or alternatively, a source of aspiration may be coupled to the guide catheter 80 and activating to pull the captured material 90 into the guide catheter 80 and from the patient's body. For example, the aspiration may pull the material 90 through the openings 47 in the basket device 40, thereby breaking the material 90 into smaller portions that may be more easily drawn into the guide catheter 80. This aspiration may also be enhanced by delivering a solvent or other therapeutic agent via the guide catheter 80 to further break up or dissolve the material 90.

With the material 90 aspirated and/or the basket device 40 partially or entirely withdrawn into the guide catheter 80, the guide catheter 80 and any remaining components of the apparatus 10 may be removed from the body lumen 92 and/or the patient's body. The process may be repeated, as desired, using the same apparatus 10 or a different apparatus (not shown). For example, the basket device 40 may be withdrawn into the sheath 30 and then directed to another location within the body lumen 92 or other elsewhere, and then redeployed to capture additional material, and the process may be repeated as often as desired. Alternatively, another apparatus 10 may be introduced into the body lumen 92 or other location before closing the entry site, as desired.

Figure 3:
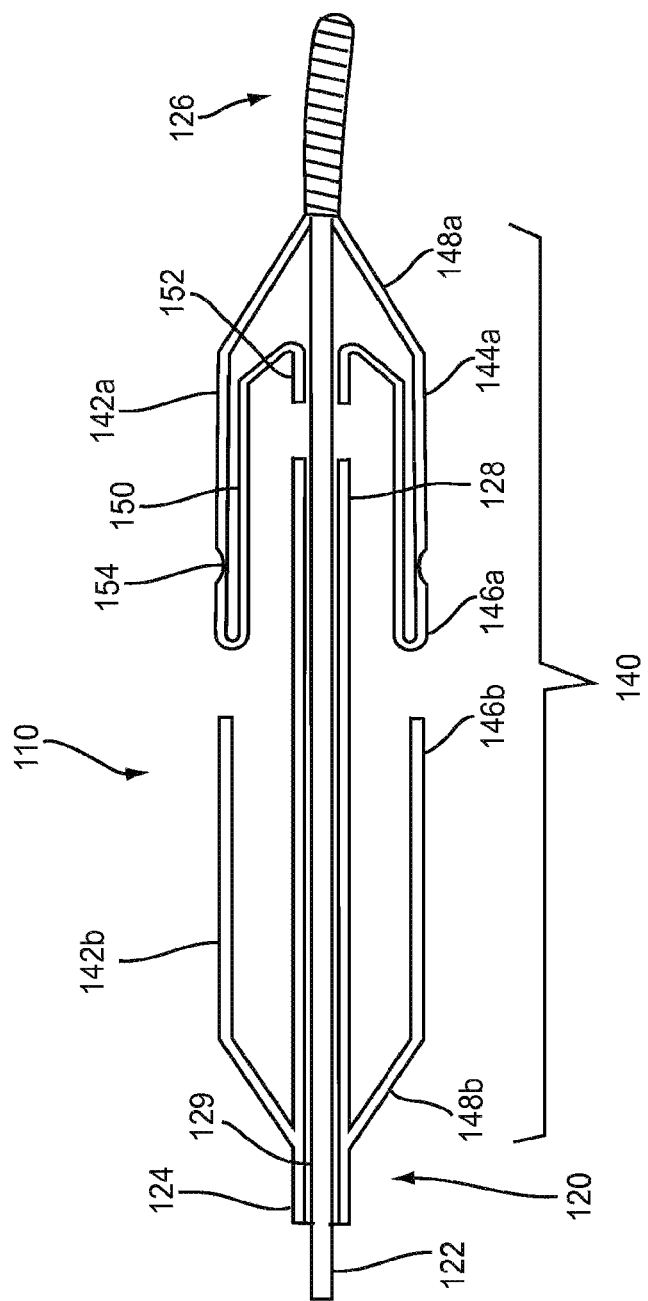
FIG. 3 is a side view of a distal end of a second embodiment of an apparatus for capturing material from within a body lumen.
Figure 4A:
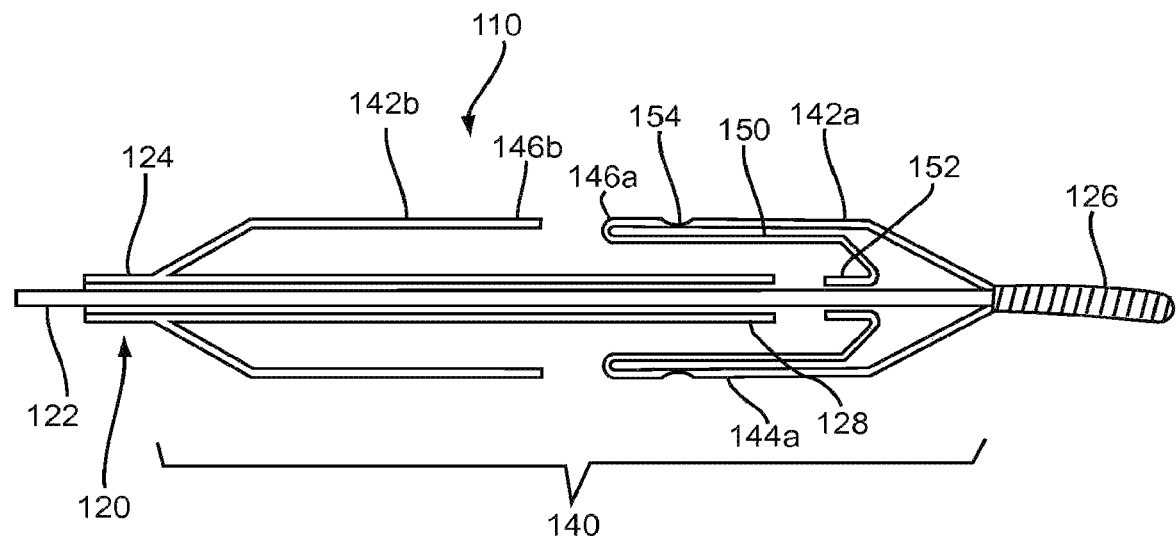
FIGS. 4A-4D are side views of the distal end of the apparatus of FIG. 3, showing actuation of the apparatus to collapse a distal basket of the apparatus and capture a portion of the distal basket within a proximal basket.
Figure 4B:
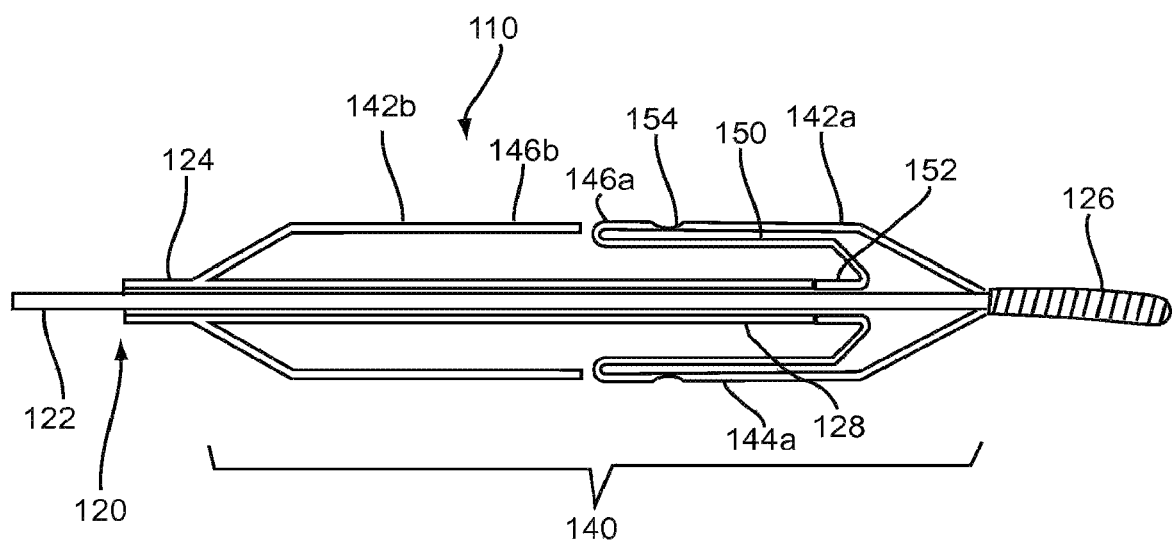
Figure 4C:
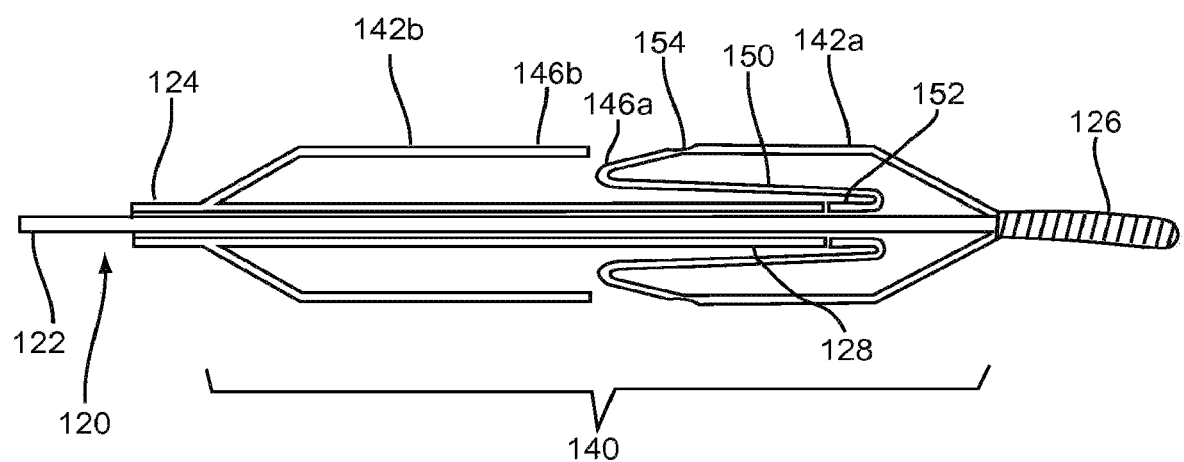
Figure 4D:
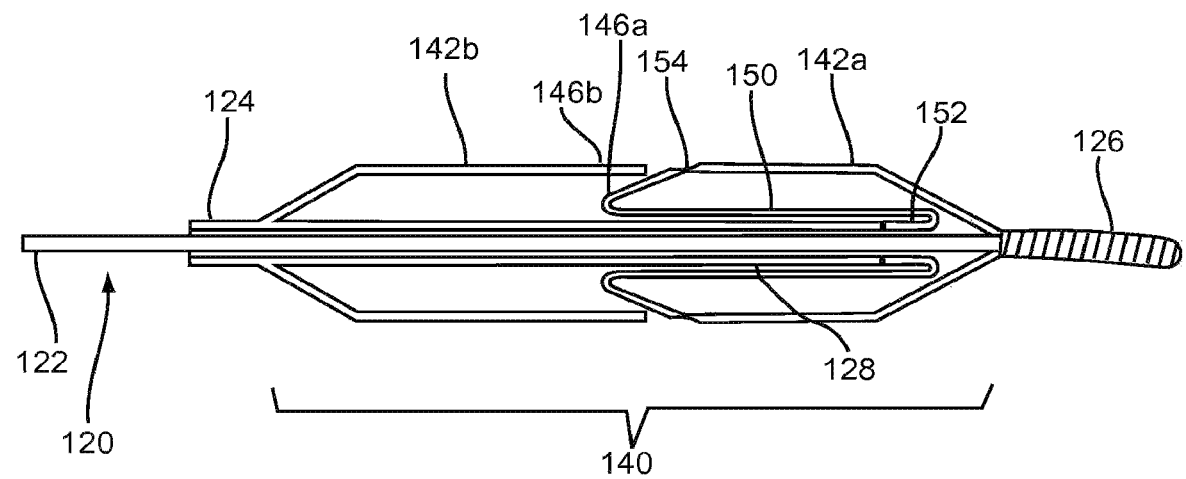

Turning to FIGS. 3-4D, another embodiment of an apparatus 110 is shown for removing, retrieving, or otherwise capturing material within a body lumen. Generally, the apparatus 110 includes an expandable basket device 140 carried by a shaft or other elongate member 120, and a sheath, micro-catheter, or other tubular member 130 (not shown, see, e.g., FIGS. 5A-5E) for facilitating delivery and/or removal of the shaft 120 and basket device 140, similar to the previous embodiments. For example, the shaft 120 includes a core wire 122 and an actuator member 124 disposed adjacent the core wire 122 that are movable axially relative to one another. The core wire 122 may be a substantially flexible elongate member terminating in a distal tip 126, and the actuator member 124 may be an elongate tubular body including a proximal end (not shown), a distal end 128 having a size for introduction into a body lumen, and a lumen 129 for slidably receiving the core wire 122 therein, e.g., also similar to the previous embodiments.

The basket device 140 carried by the shaft 120 generally includes a distal basket 142a adjacent the distal tip 126, and a proximal basket 142b proximal to and spaced apart from the distal basket 142a. For example, the distal basket 142a may be attached to or otherwise fixed axially relative to the core wire 122, e.g., adjacent the distal tip 126, and the proximal basket 142b may be attached to or otherwise fixed axially relative to the actuator member 124, e.g., to the distal end 128.

As shown in FIG. 3, each of the baskets 142 includes a circumferential wall 144 defining an open end 146 communicating with an interior of the basket 142 and a closed end 148 attached to the core wire 122 or actuator member 124. The open ends 144 are oriented towards one another and initially spaced apart from one another, as shown in FIG. 3, and the closed ends 148 are oriented away from one another. When the actuator member 124 and core wire 122 are moved axially relative to one another, one or the baskets 142 may be moved towards the other for substantially enclosing the interiors of the baskets 142, e.g., as shown in FIGS. 4A-4D and described further below.

Also similar to the previous embodiment, the baskets 142 may be expandable from a contracted condition (not shown), e.g., sized for introduction through a patient's vasculature or other passages into a body lumen, and an expanded condition (shown in FIG. 3), e.g., for capturing material within the interiors of the baskets 142. For example, the baskets 142 may be formed from elastic or superelastic material, such that the baskets 142 may be compressed radially inwardly to the contracted condition and resiliently expand towards the expanded condition, similar to the previous embodiments.

The wall 144 of the baskets 142 may be porous or otherwise include a plurality of openings 147 therein, e.g., to allow fluid to flow around and/or through the baskets 142 during use, similar to the previous embodiments. For example, as best seen in FIGS. 5C-5F, the baskets 142 may include a plurality of struts 145 surrounding openings 147. The baskets 142 may be formed from one or more hypotubes or other tubular material, e.g., by laser-cutting or otherwise removing material to define the struts 145 and openings 147, or formed from one or more wires that are cut, bent, or otherwise formed into the desired mesh structure for the baskets 142b, similar to the previous embodiments.

Unlike the previous embodiments, the distal basket 142a includes one or more elements 150 extending from the open end 146a to a collar 152 slidable on the core wire 122. For example, the elements 150 may include a plurality of struts extending from the open end 146a longitudinally along the inside of the wall 144a of the distal basket towards the closed end 148a, and then bending or curving inwardly to the collar 152. As shown, the elements 150 include at least two struts spaced apart about the circumference of the distal basket 142a, although only one or several struts may be provided, as desired. Thus, the elements 150 may couple the open end 146a to the collar 152 without substantially obstructing the interior of the distal basket 142a. Alternatively, the elements 150 may extend diagonally or radially inwardly (not shown) from the open end 146a to the collar 152, as long as the elements 150 allow the distal basket 142a to be compressed and expanded between the contracted and expanded conditions.

The collar 152 may be slidable disposed around the core wire 122, while the closed end 148a of the distal basket 142a is substantially fixed to the core wire 122. Thus, the collar 152 may be slidable distally towards the closed end 148a to direct the open end 146a radially inwardly, as described further below.

In one embodiment, the distal basket 142a, elements 150, and collar 152 may be integrally formed from a single structure, e.g., a laser-cut tube with the collar 152 and elements 150 initially extending axially beyond the open end 146a of the distal basket 142 (not shown). The collar 152 and elements 150 may then be bent or otherwise deformed to position the collar within the interior of the distal basket 142a and the elements along the inside of the wall 144a, and the material heat treated or otherwise to program the desired shape. Alternatively, the collar 152, elements, 150, and/or distal basket 142a may be formed from separate components that are attached together, e.g., by welding, bonding, and the like.

Also unlike the previous embodiments, the proximal basket 142b is attached to the actuator member 124 proximal to the distal end 128. For example, as shown in FIG. 3, the closed end 148b of the proximal basket 142b may be attached to the actuator member 124 proximal to the distal end 128 of the actuator member 124, e.g., such that the distal end 128 extends distally at least partially through the interior of the proximal basket 142b. Alternatively, a separate tubular member or other feature (not shown) may be attached to the closed end 148b of the proximal basket 142b and/or to the distal end 128 of the actuator member 124 such that the feature extends axially through the proximal basket 142b. The distal 128 (or separate feature) may extend distally over the core wire 122 through the interior of the proximal basket 142b towards the interior of the distal basket 142a. For example, as shown in FIG. 3, the distal end 128 of the actuator member 124 may extend into the interior of the distal basket 142a such that the distal end 128 is adjacent but spaced apart from the collar 152.

Turning to FIGS. 4A-4D, the distal end 128 of the actuator member 124 and collar 152 may provide a mechanism for compressing the open end 146a of the distal basket 142a during use. For example, as shown in FIG. 4A, the distal end 128 of the actuator member 124 may be spaced apart from the collar 152 by a distance that is less than the distance between the open ends 146 of the distal and proximal baskets 142. Although the open ends 146 of the baskets 142 are shown to be relatively close to one another compared to the length of the baskets 142, it will be appreciated that the spacing is not shown to scale, and that the open ends 146 may be spaced apart any desired distance, e.g., to accommodate receiving material between the baskets 142 during use, as described elsewhere herein.

As shown in FIG. 4B, when the core wire 122 is pulled proximally relative to the actuator member 124 (or the actuator member 124 is advanced distally) to direct the baskets 142 towards one another, the distal end 128 and collar 152 may contact one another before the open ends 146 of the baskets 142 contact one another, i.e., the open ends 146 may yet be spaced apart from one another. As the core wire 122 or actuator member 124 is actuated further, the distal end 128 may contact the collar 152 and cause the collar 152 to be directed towards the closed end 148a of the distal basket 142a, as shown in FIG. 4C. This action applies tension to the elements 150 coupled to the open end 146a of the distal basket 142a, thereby applying a radially inward force on the open end 146a.

As shown, thinned or weakened regions, hinges, or other bend features 154 may be provided on the struts of the distal basket 142a adjacent to the open end 146a. For example, the struts defining the circumferential wall 144a of the distal basket 142a may have their width and/or thickness reduced relative to the other struts, e.g., by machining, etching, and the like. These preferential bend features 154 may cause the distal basket 146a to bend inwardly at these features 154, as shown in FIG. 4C. Alternatively, if no bend features 154 are provided, the distal basket 142a may bend inwardly at other locations along the circumferential wall 144a, e.g., at the transition between the closed end 148a and the circumferential wall 144a (not shown). Thus, the deformation of the distal basket 142a may be distributed along its longitudinal length, or it may be concentrated at the preferential bend features 154.

Turning to FIG. 4D, as the core wire 122 or actuator member 124 are actuated further, the axial positions of the baskets 142 continue to converge, and as the open end 146a of the distal basket 142 deforms radially inward, the open ends 146 begin to overlap. For example, the open end 142a of the distal basket 142 may be deformed radially inwardly until it contacts the actuator member 124, although the open end 142a may be spaced radially away from the actuator member 124, if desired. As shown, the degree of inward radial deformation of the open end 146a of the distal basket 142a may be sufficient such that the open end 142a may extend into the open end 146b of the proximal basket 142b. In doing so, the edges of the open end 146a of the distal basket 142a may be presented as the basket device 140 is retracted, e.g., into the delivery sheath 130 (see, e.g., FIGS. 5A-5E), guide catheter 80, or other device, and/or removed from the body lumen 92 and/or the patient's body.

In addition, the overlap of the proximal basket 142b partially over the distal basket 142a may facilitate directing the basket device 140 back to the contracted condition, e.g., to facilitate removal. For example, if the basket device 140 in the configuration shown in FIG. 4D is retracted into the guide catheter 80, as shown in FIG. 5F (or, alternatively, into the delivery sheath 130 or other device, not shown), the closed end 148b of the proximal basket 142b may be tapered to allow the proximal basket 142b to be compressed radially inwardly as it is drawn into the guide catheter 80. The open end 146b of the proximal basket 142b may press inwardly against the open end 146a of the distal basket 142a, thereby causing the distal basket 142a to also be compressed radially inwardly. Optionally, the baskets 142 may be compressed inwardly back to the original contracted condition or other size sufficiently small to allow withdrawal partially or entirely into the guide catheter 80.

Turning to FIGS. 5A-5F, an exemplary method is shown for retrieving, removing, or otherwise capturing material 90 within a body lumen 92 using the apparatus 110. Similar to the previous methods, the material 90 may be a foreign body, or a result of undesirable biological processes such as thrombus within the vasculature or stones within the urinary tract.

Figure 5A:
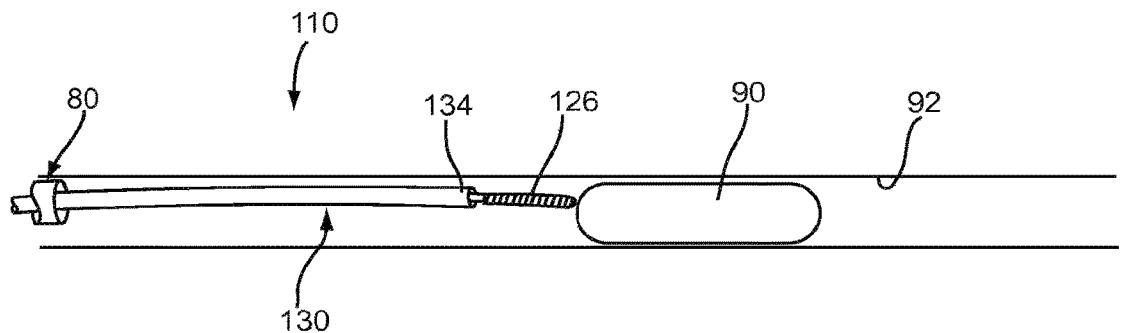
FIGS. 5A-5F are cross-sectional views of a body lumen showing a method for capturing material from the body lumen using the apparatus of FIG. 3.
Figure 5B:
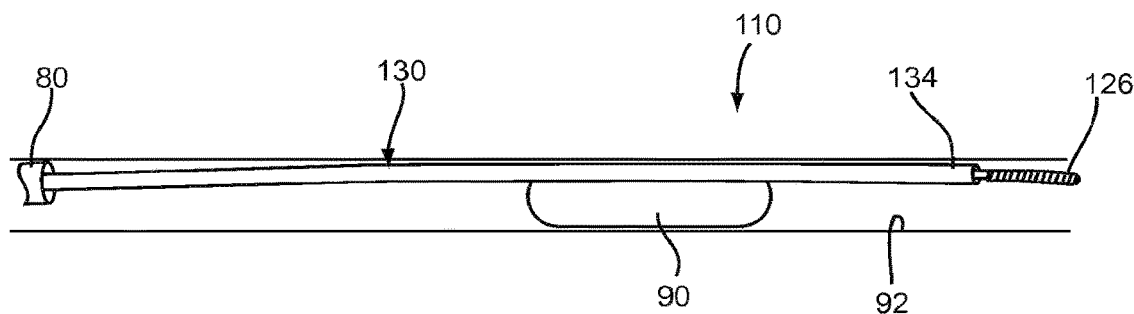

Initially, as shown in FIG. 5A, the apparatus 110 is provided within the basket device 140 (not shown, see FIGS. 5C-5F) within the sheath 130 in the contracted condition. The apparatus 110 has been advanced through a guide catheter 80 into the body lumen 92 such that the distal tip 126 is adjacent the material 90. Turning to FIG. 5B, the apparatus 110 may be advanced at least partially past the material 90, e.g., such that the distal tip 126 and the distal basket 142a (not shown) within the sheath 130 is positioned distally beyond the material 90. Similar to the previous embodiments, the relatively low profile of the sheath 130 and atraumatic distal tip 126 may facilitate advancing the apparatus 100 adjacent or through the material 90 without substantial risk of dislodging, breaking, or otherwise damaging the material 90.

Optionally, the guide catheter 80 and/or sheath 130 may facilitate delivering one or more fluids into the body lumen 92, e.g., to facilitate imaging and/or positioning the apparatus 110 and/or material 90, similar to the previous embodiments. For example, markers (not shown) may be provided on the apparatus 110 to facilitate positioning the basket device 140 relative to the material 90 before deployment, also similar to the previous embodiments.

Figure 5C:
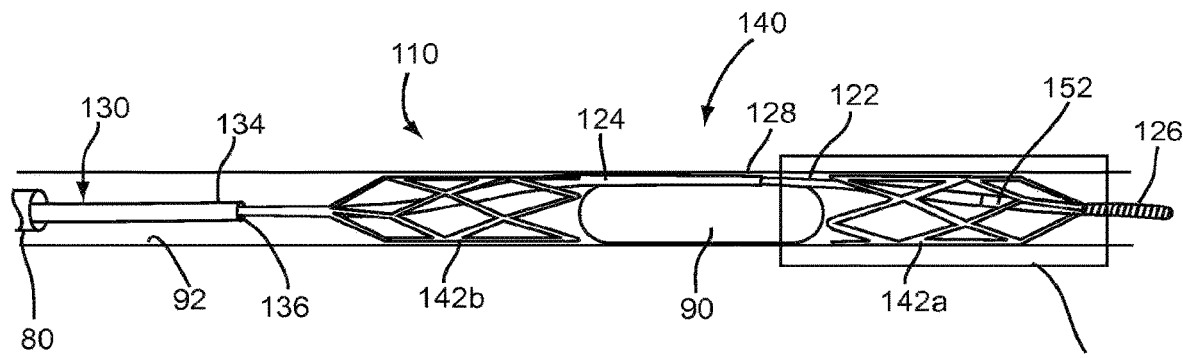

Turning to FIG. 5C, the basket device 140 may then be deployed within the body lumen 92, e.g., such that the material to be removed or captured is disposed within or adjacent the basket device 140. For example, with the distal end 134 of the sheath 130 disposed adjacent or distally beyond the material, the core wire 122 may be advanced, thereby deploying the distal basket 142a beyond the material 90. With the proximal basket 142b remaining within the sheath 130, the apparatus 110 may be manipulated further, e.g., to position the distal basket 142a immediately adjacent the material 90 and/or with the material 90 at least partially captured within the open end 146a of the distal basket 142a.

The proximal basket 142b may then be deployed proximal to the material 90, e.g., by retracting the sheath 130 or advancing the actuator member 134. As described above, the baskets 142 may resiliently and/or automatically expand upon being exposed within the body lumen 92. In the expanded condition, the open ends 146 may substantially engage or contact the wall of the body lumen 92, e.g., to prevent material 90 captured between the proximal and distal baskets 142 from being released.

Figure 5D:
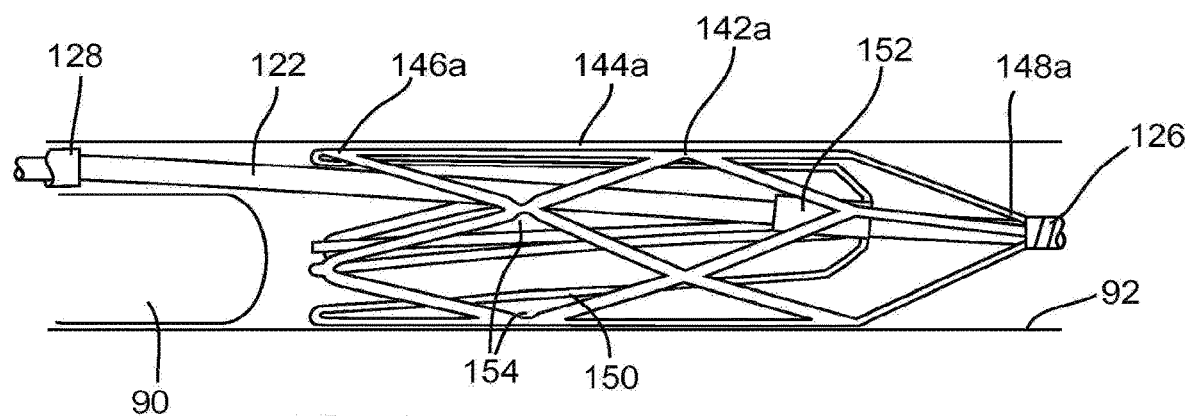

As can be seen in FIG. 5D, the core wire 122 extends through the interior of the distal basket 142a with the collar 152 free to slide along the core wire 122 to accommodate expansion of the open end 146a of the distal basket 142a. The distal end 128 of the actuator member 124 is spaced substantially away from the collar 152, i.e., proximally beyond the open end 146a of the distal basket 142a since the proximal basket 142b is positioned a substantial distance proximal to the distal basket 142a. As shown, the core wire 122 may be disposed in a generally concentric position with respect to the body lumen 92 and the baskets 142. Alternatively, if desired, the core wire 122 may be positioned in an eccentric position, e.g., by modifying the shape of the closed ends 148 of the baskets 142, such that the core wire 122 extends along one side of the walls 144 of the baskets 142 (not shown).

Figure 5E:
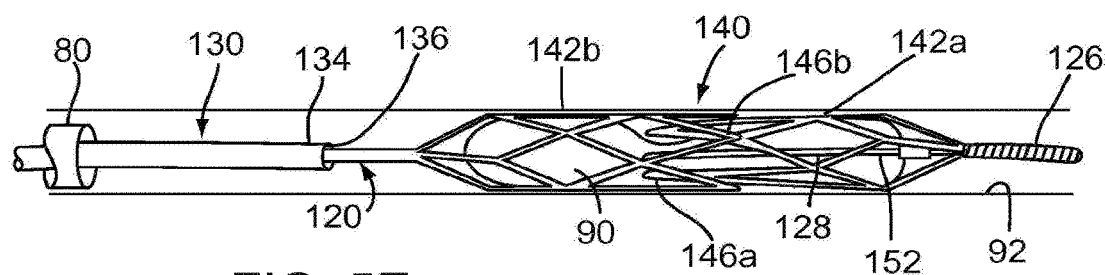
Figure 5F:
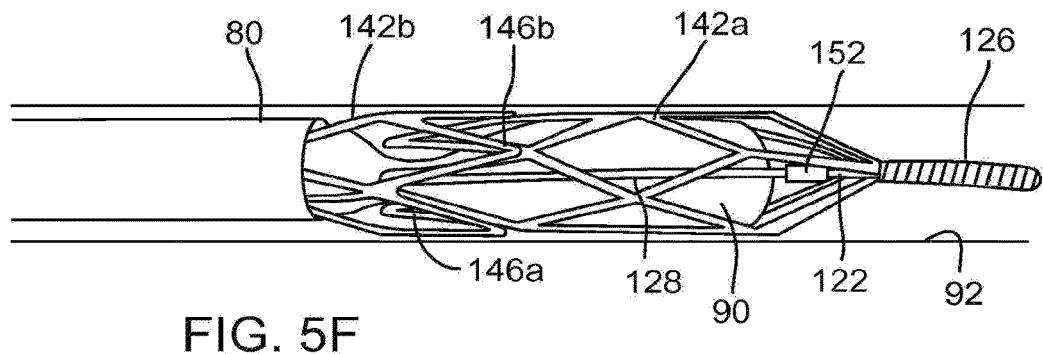

Turning to FIG. 5E, the basket device 140 may then be actuated to capture the material 90 within the baskets 142, e.g., to minimize liberation of the material 90 during removal. For example, the actuator member 124 may be advanced distally to direct the proximal basket 142b distally towards the distal basket 142a, e.g., to capture material 90 within the interior of the baskets 142. In particular, with additional reference to FIGS. 4A-4D, the actuator member 124 may be advanced until the distal end 128 of the actuator member 122 contacts and pushes the collar 152 distally, thereby compressing the open end 146a of the distal basket 142a radially inwardly and into the open end 146b of the proximal basket 14b. Thus, as shown in FIG. 5E, as a result, the material 90 may be substantially captured within the baskets 142 to minimize risk of release of the material 90.

Finally, as shown in FIG. 5F, the apparatus 110 may then be withdrawn from the body lumen 92 along with the material 90 captured within the basket device 140. For example, as shown, the apparatus 110 may be pulled until the basket device 140 is at least partially received within the guide catheter 80. As the proximal basket 142*b* contacts the guide catheter 80, the proximal basket 142*b* may be compressed radially inwardly towards the contracted condition as it is pulled into the guide catheter 80. As this motion continues, the distal basket 142*a* may also be withdrawn into the guide catheter 80 without hanging up because the leading edge of the open end 146*a* is contained within the proximal basket 142*b*, and thus does not present any sharp or blunt edges. Furthermore, none of the struts or leading edges of the open end 146*a* of the distal basket 142*a* are likely to protrude through the openings 147*b* of the proximal basket 142*b* because they are radially deformed inwardly toward the core wire 122.

The guide catheter 80 with the apparatus 110 therein may be withdrawn from the body lumen 92 and entirely from the patient's body with the baskets 142 completely contained within the guide catheter 80. Alternatively, if desired, the basket device 140 may only be partially withdrawn into the guide catheter 80 before removal from the patient's body. In a further alternative, the apparatus 110 may be removed from the body lumen 92 and/or entirely from the patient's body without withdrawing the basket device 140 into the guide catheter 80. In this alternative, bending and capturing the open end 146*a* of the distal basket 142*a* within the proximal basket 142*b* may ensure that no blunt or sharp edges are presented on the leading edge of the distal basket 142*a*, which may facilitate retracting the apparatus 110 through other devices (such as an arterial access introducer sheath, not shown) or otherwise along the delivery path through the patient's vasculature, e.g., along various body lumens and/or tissue punctures through which the apparatus 110 was originally tracked when accessing the target body lumen 92.

Optionally, one or more therapeutic agents may be delivered and/or fluid may be aspirated at any time via the guide catheter 80 or component of the apparatus 110, similar to the previous embodiments.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

The invention claimed is:

1. A method for removing material within a body lumen of a patient, the method comprising:
   introducing a basket device into the body lumen in a contracted condition, the basket device comprising a proximal basket and a distal basket spaced apart from one another, each of the proximal and distal baskets comprising an open end communicating with an interior of the respective basket, the open ends oriented towards one another;
   deploying the distal basket such that the distal basket expands within the body lumen and the open end is disposed distal to material to be removed;
   deploying the proximal basket such that the proximal basket expands within the body lumen and the open end is disposed proximal to material to be removed; and
   directing at least one of the proximal and distal baskets towards the other to capture the material through the open ends into interiors of the proximal and distal baskets;
   wherein the basket device comprises a middle portion extending between the proximal and distal baskets, the middle portion being disposed adjacent the material to be removed after deploying the proximal and distal baskets;
   wherein the middle portion is axially compressed when the at least one of the proximal and distal baskets is directed towards the other; and
   wherein the middle portion is coupled to the open ends of the proximal and distal baskets by a plurality of struts, the struts deforming when the at least one of the proximal and distal baskets is directed towards the other to accommodate receiving the middle portion within the interiors of the proximal and distal baskets.

2. The method of claim 1, wherein the basket device is introduced into the body lumen via a tubular member, the tubular member constraining the proximal and distal baskets in the contracted condition.

3. The method of claim 2, wherein:
   deploying the distal basket comprises exposing the distal basket from the tubular member within the body lumen, the distal basket resiliently expanding from the contracted condition to an expanded condition within the body lumen; and
   deploying the proximal basket comprises exposing the proximal basket from the tubular member within the body lumen, the proximal basket resiliently expanding from the contracted condition to the expanded condition within the body lumen.

4. The method of claim 3, wherein the open ends of the proximal and distal baskets contact a wall of the body lumen in the expanded condition.

5. The method of claim 1, wherein the middle portion comprises a porous member for at least partially engaging the material disposed between the proximal and distal baskets.

6. The method of claim 1, wherein the open end of the distal basket is directed radially inwardly as the at least one of the proximal and distal baskets are directed towards the other.

7. The method of claim 6, wherein the at least one of the proximal and distal baskets is directed towards the other until the open end of the distal basket is directed radially inwardly and received within the open end of the proximal basket.

8. The method of claim 7, further comprising:
   directing the proximal basket at least partially into a lumen of a tubular device; and
   withdrawing the tubular device from the body lumen with the proximal basket at least partially directed into the lumen of the tubular device.

9. The method of claim 8, wherein the proximal basket is directed entirely into the lumen of the tubular device, the proximal basket being compressed radially inwardly as the proximal basket is directed into the lumen of the tubular device.

10. The method of claim 8, wherein the proximal basket at least partially compresses the distal basket radially inwardly when the proximal basket is directed into the lumen of the tubular device.

11. The method of claim 10, wherein the distal basket is directed into the lumen of the tubular device after the proximal basket is directed into the lumen of the tubular device.

12. The method of claim 11, wherein the open ends of the proximal and distal baskets are at least partially entwined with one another when the at least one of the proximal and distal baskets is directed towards the other, thereby securing the material within the baskets.

13. A method for removing material within a body lumen of a patient, the method comprising:
    introducing a basket device into the body lumen in a contracted condition, the basket device comprising a proximal basket and a distal basket spaced apart from one another, each of the proximal and distal baskets comprising an open end communicating with an interior of the respective basket, the open ends oriented towards one another;
    deploying the distal basket such that the distal basket expands within the body lumen and the open end is disposed distal to material to be removed;
    deploying the proximal basket such that the proximal basket expands within the body lumen and the open end is disposed proximal to material to be removed; and
    directing at least one of the proximal and distal baskets towards the other to capture the material through the open ends into interiors of the proximal and distal baskets;
    wherein the open end of the distal basket is directed radially inwardly as the at least one of the proximal and distal baskets are directed towards the other; and
    wherein the at least one of the proximal and distal baskets is directed towards the other until the open end of the distal basket is directed radially inwardly and received within the open end of the proximal basket.

14. The method of claim 13, further comprising:
    directing the proximal basket at least partially into a lumen of a tubular device; and
    withdrawing the tubular device from the body lumen with the proximal basket at least partially directed into the lumen of the tubular device.

15. The method of claim 14, wherein the proximal basket is directed entirely into the lumen of the tubular device, the proximal basket being compressed radially inwardly as the proximal basket is directed into the lumen of the tubular device.

16. The method of claim 14, wherein the proximal basket at least partially compresses the distal basket radially inwardly when the proximal basket is directed into the lumen of the tubular device.

17. The method of claim 16, wherein the distal basket is directed into the lumen of the tubular device after the proximal basket is directed into the lumen of the tubular device.

18. The method of claim 17, wherein the open ends of the proximal and distal baskets are at least partially entwined with one another when the at least one of the proximal and distal baskets is directed towards the other, thereby securing the material within the proximal and distal baskets.

19. The method of claim 13, wherein the basket device is introduced into the body lumen via a tubular member, the tubular member constraining the proximal and distal baskets in the contracted condition.

20. The method of claim 13, wherein the basket device comprises a middle portion extending between the proximal and distal baskets, the middle portion comprising a porous member for at least partially engaging the material disposed between the proximal and distal baskets.

\* \* \* \* \*